(12) United States Patent
Hara et al.

(10) Patent No.: US 9,114,070 B2
(45) Date of Patent: Aug. 25, 2015

(54) LIPOSOME FOR DELIVERY TO POSTERIOR SEGMENT OF EYE AND PHARMACEUTICAL COMPOSITION FOR DISEASE IN POSTERIOR SEGMENT OF EYE

(75) Inventors: Hideaki Hara, Nara (JP); Hirofumi Takeuchi, Gifu (JP)

(73) Assignee: NAGOYA INDUSTRIAL SCIENCE RESEARCH INSTITUTE, Aichi (JP)

( * ) Notice: Subject to any disclaimer, the term of this patent is extended or adjusted under 35 U.S.C. 154(b) by 523 days.

(21) Appl. No.: 12/919,807

(22) PCT Filed: Feb. 26, 2009

(86) PCT No.: PCT/JP2009/053609
§ 371 (c)(1),
(2), (4) Date: Aug. 27, 2010

(87) PCT Pub. No.: WO2009/107753
PCT Pub. Date: Sep. 3, 2009

(65) Prior Publication Data
US 2011/0008421 A1      Jan. 13, 2011

(30) Foreign Application Priority Data
Feb. 29, 2008   (JP) .................................. 2008-051427

(51) Int. Cl.
*A61K 9/127*     (2006.01)
*A61K 9/00*      (2006.01)
*A61K 31/00*     (2006.01)

(52) U.S. Cl.
CPC .............. *A61K 9/0048* (2013.01); *A61K 9/1272* (2013.01); *A61K 31/00* (2013.01)

(58) Field of Classification Search
CPC ..................................................... A61K 9/127
USPC ....................................................... 424/450
See application file for complete search history.

(56) References Cited

U.S. PATENT DOCUMENTS

| | | | |
|---|---|---|---|
| 4,938,965 | A | 7/1990 | Shek et al. |
| 5,945,121 | A | 8/1999 | Kato et al. |
| 8,097,276 | B2 | 1/2012 | Kogure et al. |
| 2005/0089545 | A1 | 4/2005 | Kuwano et al. |
| 2009/0136563 | A1 | 5/2009 | Kogure et al. |

FOREIGN PATENT DOCUMENTS

| | | |
|---|---|---|
| CN | 1568939 | 1/2005 |
| CN | 1593437 | 3/2005 |
| CN | 101107069 | 1/2008 |
| EP | 1334718 | 8/2003 |
| JP | 10-067688 | 3/1998 |
| JP | 2003-313119 | 11/2003 |
| JP | 3624418 | 12/2004 |
| JP | 3963506 | 6/2007 |
| JP | 2007-224032 | 9/2007 |
| WO | 90/11781 | 10/1990 |
| WO | 2005/048986 | 6/2005 |

OTHER PUBLICATIONS

Sun, K.X. et al., Preparation of diclofenac sodium liposomes and its ocular pharmacokinetics, Acta Pharmaceutica Sinica, 2006, 41(11), 1094-1098.
Foreign Medical Sciences, Section of Ophthalmology, 1982, vol. 16, No. 2, 80-83.
Journal of Guangzhou, University of Traditional Chinese Medicine, 1996, vol. 13, Nos. 3 and 4, 51-54.
Journal of Otolaryngology and Ophthalmology of Shandong University, 2007, vol. 21, No. 3, 255-259.
Chinese Office Action dated Dec. 2, 2011, from the Chinese Patent Office in corresponding Chinese Application No. 200980106655.4, and English translation thereof.
Anonymous, Transdermal & topical delivery, 2003, Pharmaceutical Press, pp. 124-125.
Supplementary European Search Report dated Jun. 12, 2013 for EP Patent Application No. 09714964.5.
Hironaka, K. et al., Koganbu Sotatsu o Mezashita Liposome Tengan Seizai no Sekkei, Abstracts of 128th Annual Meeting of Pharmaceutical Society of Japan, Mar. 5, 2008, No. 4, p. 112, 26O-am02.
Matsuo, T. et al., Biochemical and Biophysical Research Communications, 1996, vol. 219, p. 947-950.
International Search Report for PCT/JP2009/053609.

*Primary Examiner* — Zohreh Fay
(74) *Attorney, Agent, or Firm* — Roylance, Abrams, Berdo & Goodman, L.L.P.

(57) ABSTRACT

The invention provides a liposome for delivery to the posterior segment of the eye, comprising (A) a phospholipid, (B) a charged substance, and/or (C) a membrane-reinforcing substance; the liposome having a rigidity that provides the liposome with cell membrane permeability, and having a mean particle diameter of 1 µm or less; and a pharmaceutical composition for a disease in the posterior segment of an eye, comprising a drug encapsulated in the liposome. The liposome is delivered to the posterior segment of the eye by instillation, and is non-cytotoxic; and the pharmaceutical composition for a disease in the posterior segment of the eye comprises the liposome.

6 Claims, 17 Drawing Sheets

Elapsed Time after Instillation of DSPC ssLip of Example 3

Bar : 25 μm

**Ex. 8: DSPC ssLip
(Mean Particle Diameter 116.8 nm)**

Ex. 9: DSPC ssLip
(Mean Particle Diameter 174.8 nm)

Ex. 10: DSPC ssLip
(Mean Particle Diameter 300.6 nm)

Ex. 11: DSPC ssLip
(Mean Particle Diameter 561.0 nm)

Ex. 12: EPC ssLip (H/P=0.15)

Ex. 13: DSPC ssLip (A+B+C)

Ex. 14: DSPC ssLip (A+B)

Ex. 15: DSPC ssLip (A+B+C)

Ex. 16: DSPC ssLip (A+C)

Comp Ex. 3: FITC-labeled Polystyrene Particles
(H/P=1.0)

Ex. 5 DPPC ssLip (Mean Particle Diameter 114.1 nm)

Ex. 6: DMPC ssLip (Mean Particle Diameter 124.7 nm)

LIPOSOME FOR DELIVERY TO POSTERIOR SEGMENT OF EYE AND PHARMACEUTICAL COMPOSITION FOR DISEASE IN POSTERIOR SEGMENT OF EYE

TECHNICAL FIELD

The present invention relates to a liposome capable of delivery to the posterior segment of the eye, and to a pharmaceutical composition for a disease in the posterior segment of the eye that comprises the liposome.

BACKGROUND ART

Conventionally, invasive methods such as subconjunctival or intravitreal injections are widely used for drug treatments for diseases in the posterior segment of the eye.

This is partly because topical administration to the eye, such as instillation, results in a short drug residence time due to tears and the like, or results in low drug permeability into corneal and conjunctival epithelial cells.

However, there are problems with injections such as a lack of ease of administration, and concerns about complications such as vitreous hemorrhage and retinal detachment. Hence, there is a need for a drug that is highly capable of being delivered to the posterior segment of the eye via non-invasive methods of administration, such as local administration to the eye.

Several attempts have been made to utilize liposomes for local administration to the eye; however, such attempts have been made solely for the purpose of extending residence time on the corneal surface (Patent Literature 1), and the like. Thus, there have been no successful results for delivery of a drug to the posterior segment of the eye by local administration of a liposome to the eye.

Patent Document 2 discloses a liposome preparation intended for delivery into the retinal cells, reporting that the "DNA encapsulated" in a specific liposome containing dilauroylphosphatidylcholine (DLPC) or dioleoylphosphatidylethanolamine (DOPE) could be delivered to the retinal ganglion cells. This liposome, however, does not encapsulate a chemical substance.

The "Detailed Description of the Invention" section of Patent Document 2 discloses various liposome compositions and preparation methods. However, among the liposomes containing phospholipids, those that were actually demonstrated to deliver the encapsulated DNA to the retinal ganglion cells were all multilamellar liposomes (multilamellar vesicles; hereinafter abbreviated as "MLVs").

As a result of unique research and development conducted by the present inventors, it has become evident that, in the case of MLVs, the liposome itself cannot be delivered to the posterior segment of the eye. That is, in Patent Document 2, although the DNA encapsulated in the liposome was delivered to the posterior segment of the eye, it is likely that the liposome itself collapses midway, and does not reach the posterior segment of the eye. This means that the proportion of the encapsulated DNA that was delivered to the posterior segment of the eye is not necessarily high.

Patent Document 1: Japanese Patent No. 3,624,418
Patent Document 2: Japanese Patent No. 3,963,506

DISCLOSURE OF THE INVENTION

Problems to be Solved by the Invention

In view of the above, the present inventors conducted more extensive research into a liposome capable of delivery to the posterior segment of the eye. Consequently, they found that, by using a liposome having a mean particle diameter in the submicron range, it is possible to prepare a liposome preparation capable of delivery to the posterior segment of the eye for use with a drug effective in preventing or treating a disease in the posterior segment of the eye. The invention has been accomplished based on this finding. An object of the invention is to provide a liposome of a novel composition that is delivered to the posterior segment of the eye by topical applications, and that is non-cytotoxic; and a pharmaceutical composition for a disease in the posterior segment of the eye that comprises the liposome.

Means for Solving the Problems

The above-mentioned object is achieved by first to tenth aspects of the invention set forth below.

First Aspect of the Invention

A liposome for delivery to the posterior segment of the eye, comprising
 (A) a phospholipid, and
 at least one selected from
 (B) a charged substance and
 (C) a membrane-reinforcing substance;
 the liposome having a rigidity that provides the liposome with cell membrane permeability, and having a mean particle diameter of 1 μm or less.

Second Aspect of the Invention

The liposome for delivery to the posterior segment of the eye according to the first aspect of the invention, wherein the rigidity that provides the liposome with cell membrane permeability has an H/P value of 0.15 to 1.0 according to Expression (I):

$$H/P \qquad (I)$$

wherein H represents a height of the liposome adsorbed on a substrate, as measured by atomic force microscopy; and P represents a mean particle diameter of the liposome, as measured by dynamic light scattering.

Third Aspect of the Invention

The liposome for delivery to the posterior segment of the eye according to the first or second aspect of the invention, wherein the mean particle diameter is 600 nm or less.

Fourth Aspect of the Invention

The liposome for delivery to the posterior segment of the eye according to any one of the first to third aspects of the invention, wherein Component (A) has acyl groups having 12 to 18 carbon atoms.

Fifth Aspect of the Invention

The liposome for delivery to the posterior segment of the eye according to any one of the first to fourth aspects of the invention, wherein Component (A) comprises at least one phospholipid selected from the group consisting of distearoylphosphatidylcholine, dipalmitoylphosphatidylcholine, dimyristoylphosphatidylcholine, dilauroylphosphatidylcholine, egg phosphatidylcholine, and hydrogenated phosphatidylcholine.

Sixth Aspect of the Invention

The liposome for delivery to the posterior segment of the eye according to any one of the first to fifth aspects of the invention, wherein liposome particles have a gel to liquid-crystalline phase transition temperature of 20° C. or more.

Seventh Aspect of the Invention

The liposome for delivery to the posterior segment of the eye according to any one of the first to sixth aspects of the invention, wherein Component (B) is a negatively charged substance.

Eighth Aspect of the Invention

The liposome for delivery to the posterior segment of the eye according to any one of the first to seventh aspects of the invention, wherein Component (C) is a compound having a steroid skeleton.

Ninth Aspect of the Invention

A pharmaceutical composition for a disease in the posterior segment of the eye, comprising a drug effective in preventing or treating the disease in the posterior segment of the eye, the drug being encapsulated in the liposome for delivery to the posterior segment of the eye according to any one of the first to eighth aspects of the invention.

Tenth Aspect of the Invention

The pharmaceutical composition for a disease in the posterior segment of the eye according to the ninth aspect of the invention, which is used in the form of an ophthalmic solution.

Effects of the Invention

The liposome of the invention has the advantage of being capable of delivery to the posterior segment of the eye, and being non-cytotoxic. Thus, the pharmaceutical composition of the invention for a disease in the posterior segment of the eye does not involve the difficulties of injections or the like, and can prevent or treat the disease in the posterior segment of the eye simply by local administration to the eye, such as instillation.

BEST MODE FOR CARRYING OUT THE INVENTION

Figure 1:
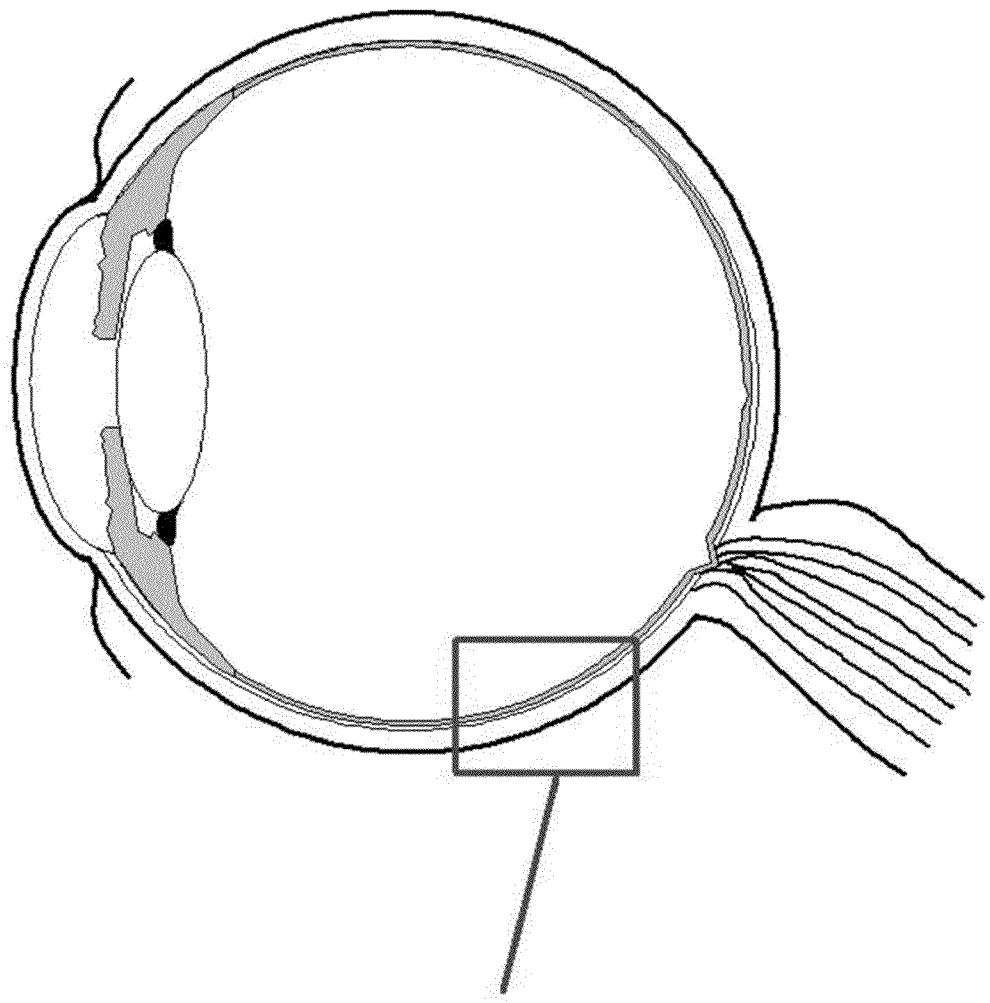
FIG. 1 is a diagram showing frozen slices of enucleated portions from eyeballs in the test for investigating delivery to the posterior segment of the eye.

Liposome of the Invention for Delivery to the Posterior Segment of the Eye

The liposome of the invention for delivery to the posterior segment of the eye contains Component (A), and at least one selected from Component (B) and Component (C) shown below. The liposome has a rigidity that provides the liposome with cell membrane permeability, and has a mean particle diameter of 1 μm or less.

(A) A phospholipid
(B) A charged substance
(C) A membrane-reinforcing substance

Components of the Liposome of the Invention for Delivery to the Posterior Segment of the Eye Each of the components is described in detail below.

(A) Phospholipid

The phospholipid used in the liposome of the invention for delivery to the posterior segment of the eye is not limited as long as it can impart rigidity to the liposome particles. For example, a relatively long phospholipid is preferred, such as a phospholipid having acyl groups with 12 to 18 carbon atoms. Specific examples of such phospholipids include distearoylphosphatidylcholine (DSPC), dipalmitoylphosphatidylcholine (DPPC), dimyristoylphosphatidylcholine (DMPC), dilauroylphosphatidylcholine (DLPC), egg phosphatidylcholine (EPC), and hydrogenated phosphatidylcholine (HyPC). Among the above, DSPC is preferred because it easily forms rigid particles.

These phospholipids can also be used alone or in combination.

In addition to Component (A), the liposome of the invention needs to contain at least one selected from Component (B) and Component (C) described below. Of Components (B) and (C), the liposome preferably contains Component (B), and particularly preferably contains both Components (B) and (C).

(B) Charged Substance

The charged substance used in the liposome of the invention for delivery to the posterior segment of the eye is not limited as long as it can enhance the dispersion stability of the liposome particles. The charged substance includes a positively charged substance and a negatively charged substance, but a negatively charged substance is preferred because of its tendency to be less cytotoxic.

Examples of positively charged substances include stearylamine (SA), didodecyldimethylammonium bromide (DDAB), and derivatives thereof.

Examples of negatively charged substances include dicetyl phosphate (DCP), dipalmitoylphosphatidylglycerol (DPPG), and derivatives thereof. Preferred among these are DCP and its derivatives.

These charged substances may be used alone or in a combination of two or more.

Alternatively, the surface of the liposome can be charged by modifying the surface with a charged polymer.

In the invention, the charged substance (B) is preferably added in a molar ratio of the charged substance (B) to the phospholipid of 0.02 to 0.3:1, and particularly preferably 0.1 to 0.3:1.

(C) Membrane-Reinforcing Substance The membrane-reinforcing substance used in the liposome of the invention for delivery to the posterior segment of the eye is not limited as long as it can reinforce the rigidity of the liposome particles. A preferred example is a compound having a steroid skeleton. Such membrane-reinforcing substances may be used alone or in a combination of two or more.

Examples of compounds having a steroid skeleton include cholesterol (Chol.) and derivatives thereof. Specific examples of such compounds include dihydrocholesterol, cholesteryl esters, cholestanol, dehydrocholesterol, cholesteryl lanolates, cholesteryl isostearate, cholesteryl 12-hydroxystearate, cholesteryl ricinoleate, cholesteryl macadamiates, phytosterol, sitosterol, stigmasterol, campesterol, lanosterol, 2,4-dihydrolanosterol, 1-O-sterol glucosides, 1-O-sterol maltosides, and 1-O-sterol galactosides.

In the invention, the membrane-reinforcing substance (C) is preferably added in a molar ratio of the membrane-reinforcing substance (C) to the phospholipid of 0.1 to 0.3:1.

The membrane-reinforcing substance (C) has the advantage of easily forming a homogenous liposome when added as a liposome component.

The liposome of the invention may optionally contain other components, as long as it can maintain its rigidity.

Rigidity of the Liposome Particles of the Invention for Delivery to the Posterior Segment of the Eye The liposome particles of the invention need to have a rigidity that provides the liposome with cell membrane permeability. As used herein, "rigidity that provides the liposome with cell membrane permeability" means a rigidity such that the liposome can be incorporated into a cell without collapsing. The rigidity can be investigated by, for example, examining the in vitro interaction between the liposome and human corneal epithelial cells (HCE-T).

Specifically, a solution of the liposome is added to a container seeded with immortalized human corneal epithelial cells, and incubated for a certain period of time at a certain temperature; and the cells are subsequently washed and lysed. By quantifying a label such as a fluorescent material incorporated into the liposome, the cellular uptake of the liposome, i.e., whether the liposome has cell membrane permeability or not, can be examined.

The liposome can be determined to have cell membrane permeability when the uptake of a label such as a fluorescent material is higher than the cellular uptake of a control.

A more specific testing method will be described in the Examples.

Specifically, the rigidity that provides the liposome with cell membrane permeability can also be evaluated according to, for example, the method disclosed in the following paper:

*International Journal of Pharmaceutics*, 355 (1-2), P. 203-209, 2008 May 1 (electronically published 2007 Dec. 23)

The method disclosed in this paper evaluates liposome rigidity by utilizing atomic force microscopy (AFM) and dynamic light scattering (DLS).

Specifically, a suspension of the liposome is adsorbed on a substrate, for example, mica, and the liposome is visualized based on the mode of the height (H) of the liposome within an area of 10×10 μm.

The height (H) of the liposome is determined by measuring the depths of all liposome particles within a scale of 10×10 μm on the substrate surface by AFM, and evaluating the mode based on the peak tops of the histogram using software of the AFM equipment.

AFM is preferably employed with an e-scanner capable of measurement of a maximum range of 10×10×2.5 μm. For example, the Nanoscope (registered trademark) IIIa system controller, manufactured by Digital Instruments, Inc., can be used as such an e-scanner.

During measurement of the height (H), it is preferred that a certain number of liposome particles, for example, preferably at least several tens of particles per 10×10 μm, be adsorbed within the scale of 10×10 μm, in order to obtain an accurate height (H). However, when using liposome particles whose size has been adjusted to some extent, the number of the liposome particles may be less than that defined above.

Such a number of liposome particles can be adsorbed by, for example, adjusting the liposome concentration in the liposome suspension.

After the liposome suspension has been dropped onto the substrate, it is preferably allowed to stand for, for example, about 30 minutes.

Prior to the adsorption of the liposome onto the substrate surface, the mean particle diameter (P) is measured by DLS using ZETASIZER 3000HSA (MALVERN INSTRUMENT Ltd., UK), which is capable of measuring particles with a diameter of up to 0.6 to 6,000 nm.

The ζ potential of the colloidal particles is measured by the laser Doppler method using a Zetamaster (MALVERN INSTRUMENT Ltd., UK).

The rigidity of the liposome particles can be calculated according to Formula (I):

$$H/P \tag{I}$$

The liposome of the invention for delivery to the posterior segment of the eye preferably has an H/P value of 0.15 to 1.0, and more preferably 0.3 to 1.0.

Such a rigidity can be achieved by, for example, using a phospholipid having acyl groups with 12 to 18 carbon atoms as the phospholipid forming the liposome, as stated above; by using the charged substance (B) and/or the membrane-reinforcing substance (C); or by adjusting the gel to liquid-crystalline phase transition temperature of the liposome particles to a specific value.

The term "gel to liquid-crystalline phase transition" indicates the state of a phospholipid bilayer, and the temperature at which the phospholipid bilayer undergoes the phase change is referred to as the "gel to liquid-crystalline phase transition temperature (Tc)". The higher the Tc is than the environmental temperature, the more likely that the phospholipid bilayer will maintain its capsule-shaped particle state at the environmental temperature.

Therefore, it follows that the higher the Tc is, the more rigid the liposome of the invention tends to be in the in vivo environment. In the invention, the liposome preferably has a Tc of 20° C. or more, more preferably 40° C. or more, and particularly preferably 50° C. or more.

DSPC has a Tc of about 54° C. to about 55° C.; DPPC has a Tc of about 41° C. to about 42° C.; DMPC has a Tc of about 23° C. to about 24° C.; and EPC has a Tc of about −15° C. to about −7° C.

Mean Particle Diameter of the Liposome of the Invention for Delivery to the Posterior Segment of the Eye The mean particle diameter of the liposome of the invention needs to be 1 μm or less, but is preferably 600 nm or less, more preferably 80 to 250 nm, still more preferably 90 to 220 nm, and particularly preferably 100 to 200 nm. The mean particle diameter of the liposome is a value measured by DLS, as described above.

Specifically, the mean particle diameter of the liposome is a value measured by diluting one drop of the liposome suspension taken with a Pasteur pipette with a large excess of a dispersion solvent (HEPES buffer), followed by measurement using the ZETASIZER 3000HSA (MALVERN INSTRUMENT Ltd., UK).

Structure of the Liposome of the Invention for Delivery to the Posterior Segment of the Eye It is believed that the liposome of the invention typically has a monolayer structure referred to as "SUVs" (small unilamellar vesicles), but is not necessarily limited thereto.

Method for Producing the Liposome of the Invention

The method for producing the liposome of the invention is not limited, and examples of methods include suitable combinations from among the following methods (1) and (2). Among these, a thin-film hydration-extrusion method is preferred.

(1) Thin-film hydration, reverse phase evaporation, ethanol injection, dehydration-rehydration, and the like (the production of MLVs)

Among the methods (1), thin-film hydration is preferred when encapsulating a hydrophobic drug, such as 6-cumarin used in the Examples, because the method enables uniform encapsulation.

(2) Reducing the size of MLVs (the production of ssLip (submicron-sized small unilamellar vesicles (liposomes)) by extrusion of a liposome through a membrane filter at a high pressure, sonication, freeze-thawing, French press, homogenization, and the like.

Among the methods (2), sonication and extrusion are preferred for reducing the size of a liposome, and, in particular, extrusion is preferred because it enables the size of the liposome to be more uniformly reduced.

Extrusion and sonication are desirable in that particle diameter can be easily adjusted.

Thin-film hydration is a method that is performed as follows: Basic components forming a liposome membrane are dissolved in an organic solvent such as chloroform, and the solution is subsequently subjected to a rotary evaporator to distill off the solvent by heating under reduced pressure, thereby forming a thin film on the inner side of the evaporator. The thin film is then hydrated with a phosphate buffer solution, HEPES-HBSS solution, or the like in a warm-water bath.

The drug to be encapsulated in the liposome membrane or in the interior space of the liposome can be encapsulated in the liposome as follows: when the drug is water-soluble, it is dissolved in a solution for hydration; and when the drug is water-insoluble, it is dissolved in an organic solvent together with liposome-forming components.

HEPES denotes 4-(2-hydroxyethyl)-1-piperazineethanesulfonic acid.

HBSS denotes Hank's balanced salt solution.

Pharmaceutical Composition of the Invention for a Disease in the Posterior Segment of the Eye The pharmaceutical composition of the invention for a disease in the posterior segment of the eye contains a drug that is effective in preventing or treating the disease in the posterior segment of the eye, wherein the drug is encapsulated in the liposome for delivery to the posterior segment of the eye. When the drug effective in preventing or treating the disease in the posterior segment of the eye provides the effects of any of the phospholipid (A), charged substance (B), and membrane-reinforcing substance (C), which form the liposome of the invention for delivery to the posterior segment of the eye, the drug may also function as all of, or one or more of these components.

Drugs that can be encapsulated in the liposome of the invention for delivery to the posterior segment of the eye to form the pharmaceutical composition of the invention for a disease in the posterior segment of the eye are not limited. Examples of such drugs include those effective in preventing or treating diseases in the posterior segment of the eye, as mentioned below:

bunazosin hydrochloride, timolol maleate, carteolol hydrochloride, betaxolol hydrochloride, nipradilol, isopropyl unoprostone, prostaglandin preparations (e.g., latanoprost and tafluprost), dipivefrine hydrochlorate, epinephrine, pilocarpine hydrochloride, carbachol, dorzolamide hydrochloride, acetazolamide, tiopronin, parotin, pirenoxine, glutathione, memantine, steroid preparations (e.g., fluorometholone, prednisolone, betamethasone, and dexamethasone), non-steroid preparations (e.g., indomethacin, dichlofenac sodium, and bromfenac sodium), agents for preventing or treating glaucoma, agents for preventing or treating cataract, agents for preventing or treating uveitis, optic nerve-protecting agents, eye circulation-improving agents, retinal circulation-improving agents, agents for preventing or treating diabetic retinopathy, agents for preventing or treating age-related macular degeneration, VEGF inhibitors (e.g., VEGF antibody and VEGF aptamer), angiogenesis inhibitors, and agents for preventing or treating vitreous opacity.

Non-limiting examples of diseases in the posterior segment of the eye include age-related macular degeneration, diabetic retinopathy, uveitis (sympathetic ophthalmia), glaucoma, and vitreous opacity. Any diseases resulting from lesions or causes of disease in the posterior segment of the eye are included within diseases in the posterior segment of the eye.

The pharmaceutical composition of the invention for a disease in the posterior segment of the eye can be formulated into preparations according to known methods, using, for example, the following additives: buffers (e.g., phosphate buffer, borate buffer, citrate buffer, tartarate buffer, acetate buffer, and amino acids), isotonizing agents (e.g., saccharides such as sorbitol, glucose, and mannitol, polyhydric alcohols such as propylene glycol, and salts such as sodium chloride), excipients, lubricants, binders, disintegrators, stabilizers, flavoring agents, diluents, surfactants, emulsifiers, solubilizers, absorbefacients, moisturizers, adsorbents, bulking agents, extending agents, humectants, preservatives (e.g., quarternary ammonium salts such as benzalkonium chloride and benzethonium chloride, p-hydroxybenzoate esters such as methyl p-hydroxybenzoate and ethyl p-hydroxybenzoate, benzyl alcohol, phenethyl alcohol, sorbic acid, and salts thereof, thimerosal, and chlorobutanol), and viscosity-adjusting agents (e.g., hydroxyethylcellulose, hydroxypropylcellulose, methylcellulose, hydroxypropylmethylcellulose, and carboxymethyl cellulose).

The pharmaceutical composition of the invention for a disease in the posterior segment of the eye may further contain other active ingredients in amounts such that pharmacological efficacy is not impaired.

Routes of Administration of the Pharmaceutical Composition of the Invention for a Disease in the Posterior Segment of the Eye Examples of routes of administration of the pharmaceutical composition of the invention for a disease in the posterior segment of the eye include invasive methods such as injection into the posterior segment of the eye, and non-invasive methods such as local administration to the eye by instillation, application of an ophthalmic ointment, and the like. The liposome of the invention can demonstrate the most value by local administration to the eye, such as by instillation, because it is capable of delivery to the posterior segment of the eye by instillation.

Dosage Forms of the Pharmaceutical Composition of the Invention for a Disease in the Posterior Segment of the Eye Thus, examples of dosage forms of the pharmaceutical composition of the invention for a disease in the posterior segment of the eye include ophthalmic solutions, ophthalmic ointments, and injections.

Liposome Content in the Pharmaceutical Composition of the Invention for a Disease in the Posterior Segment of the Eye The liposome content in the pharmaceutical composition of the invention for a disease in the posterior segment of the eye cannot be generally limited, since it will vary depending on the dosage form, the type of drug encapsulated in the liposome, the amount of the encapsulated drug, and the like. Therefore, the liposome content may be suitably selected within ranges such that it can be formulated into various dosage forms, while considering the dose of the drug. For example, the liposome content in the pharmaceutical composition is preferably 0.01 to 20.0 (w/w %; proportion of solids), and particularly preferably 0.1 to 1.0 (w/w %: proportion of solids), based on the entire pharmaceutical composition.

It is preferred that the pharmaceutical composition be prepared such that the drug ingredient content in the total amount of the pharmaceutical composition is preferably 0.0001 to 10 (w/v %), and more preferably 0.001 to 5 (w/v %). Specifically, in the case of an injection, the drug ingredient content is preferably 0.0002 to 0.2 (w/v %), and more preferably 0.001 to 0.1 (w/v %); and in the case of an ophthalmic solution, the drug ingredient content is preferably 0.01 to 50 (w/w %), and more preferably 0.02 to 20 (w/w %). The drug ingredient content, however, is not limited to these ranges.

Dose of the Pharmaceutical Composition of the Invention for a Disease in the Posterior Segment of the Eye The dose of the pharmaceutical composition of the invention for a disease in the posterior segment of the eye will vary depending on the route of administration, symptoms, age, body weight, dosage form of the pharmaceutical composition, and the like. The pharmaceutical composition is preferably administered once or several times a day, depending on the symptoms, in a manner such that the dose of the drug enclosed in the liposome in the pharmaceutical composition for a disease in the posterior segment of the eye is preferably 0.005 to 500 mg, and more preferably 0.1 to 100 mg, per kilogram of the body weight of a subject in need of treatment; provided that the dose of the drug per day for an adult has a lower limit of preferably 0.01 mg (more preferably 0.1 mg), and an upper limit of preferably 20 g (more preferably 2,000 mg, still more preferably 500 mg, and particularly preferably 100 mg).

EXAMPLES

Examples 1 and 2

Liposome components of each of the compositions shown in Table 1 were subjected to a rotary evaporator at about 40° C. under reduced pressure, forming a thin film on the inner side of the evaporator. The thin film was subsequently hydrated with HEPES-HBSS solution or the like in a water bath of about 60° C. to 70° C., thereby preparing MLVs. The MLVs were subjected to extrusion, producing a solution containing ssLip (Examples 1 and 2). In the invention, the membrane filter used for extrusion in the Examples was a Nuclepore track-etched polycarbonate membrane, manufactured by Whatman (Schleicher & Schuell).

The rigidity (H/P) of each of the liposomes was measured according to the method described above.

(Preparation of AP-Treated Mica)

Prior to the measurement of rigidity, mica used as the substrate was pre-treated according to the method described in Thomson, 2000, *Langmuir* 16(11), 4813-4818.

Specifically, the pre-treatment of mica was performed as follows. Cleaved mica, 3-aminopropyltriethoxysilane (hereinafter referred to as AP, molecular weight: 221.4; 2 μl), and N,N-diisopropylethylamine (hereinafter referred to as DI, molecular weight: 129.2; 1 μl) were placed in a dried petri dish, the petri dish was sufficiently tightly sealed, and allowed to stand for a predetermined period of time at room temperature. At this time, the two reaction solutions were not directly dropped onto the mica, but were each added into a lid removed from a dried centrifugal tube, and the mica surface was modified with AP by the reaction in a gaseous phase. AP was subsequently removed from the petri dish together with the lid, and the petri dish was preserved after being filled with a sufficient amount of nitrogen using nitrogen gas. The prepared AP-treated mica was used within 24 hours of preparation.

Observation of the Liposome Shapes by AFM

Two-hundred microliters of each liposome suspension diluted with distilled water to 0.02 mM, calculated as the lipid concentration, was adsorbed on the AP-treated mica, and allowed to stand for 30 minutes at room temperature. Unadsorbed fine particles were subsequently removed using distilled water, and an observation was conducted. DNP-S20 (length: 120 μm, narrow, nominal spring constant: 0.32 N/m) was used as the cantilever during measurement. The cantilever was fixed to a cell in liquid, and the shape of the fine particles was observed in the tapping mode in liquid. The scanning speed during observation was 1.0 or 2.5 Hz, depending on the scan size.

As a result, the liposome particles of Examples 1 and 2 had rigidities (H/P) of 0.81 and 0.31, respectively; therefore, the liposomes of the invention having preferable rigidities were produced.

Specifically, liposome components and a drug to be encapsulated (6-cumarin) in each of the ratios shown in Table 2 were subjected to a rotary evaporator at about 40° C. under reduced pressure, forming a thin film on the inner side of the evaporator. The thin film was subsequently hydrated with HEPES-HBSS solution or the like in a water bath of about 60° C. to 70° C., thereby preparing MLVs according to each of Comparative Examples 1 and 2.

(2) Preparation of Submicron-Sized Liposomes

The MLVs of Comparative Examples 1 and 2 prepared in "(1) Preparation of MLVs" were subjected to extrusion, producing liposome solutions containing liposomes (ssLip) having mean particle diameters of 111.7 nm (Example 3) and 112.9 nm (Example 4), respectively.

The mean particle diameters of the liposomes were measured by DLS, using ZETASIZER 3000HSA (MALVERN INSTRUMENT Ltd., UK), as described above.

TABLE 1

|  |  |  | Ex. 1 | Ex. 2 |
|---|---|---|---|---|
| Preparation Composition | (A) Phospholipid | Type | DSPC | EPC |
|  |  | Amount (mg/ml) | 32.24 | 31.54 |
|  |  | Molar Ratio | 1 | 1 |
|  | (B) Charged Substance | Type | DCP | DCP |
|  |  | Amount (mg/ml) | 5.58 | 5.58 |
|  |  | Molar Ratio | 0.25 | 0.25 |
|  | (C) Membrane-Reinforcing Substance | Type | Cholesterol | Cholesterol |
|  |  | Amount (mg/ml) | 1.97 | 1.97 |
|  |  | Molar Ratio | 0.125 | 0.125 |
| Form of Liposome After Preparation |  |  | ssLip | ssLip |
|  | Liposome Height: H (nm) |  | 125.8 | 31.3 |
|  | Liposome Mean Particle Diameter: P (nm) |  | 155.8 | 101.9 |
|  | Liposome Rigidity (H/P) |  | 0.81 | 0.31 |

Examples 3 to 7 and Comparative Examples 1 and 2

(1) Preparation of MLVs

In rigid ssLip such as those prepared in Examples 1 and 2, a drug was encapsulated to form ssLip of Examples 3 and 4.

TABLE 2

|  |  |  | Ex. 13 | Ex. 14 | Ex. 15 | Ex. 16 |
|---|---|---|---|---|---|---|
| Preparation Composition | (A) Phospholipid | Type | DSPC | DSPC | DSPC | DSPC |
|  |  | Molar Ratio | 1 | 1 | 1 | 1 |
|  | (B) Charged Substance | Type | DCP | DCP | SA | — |
|  |  | Molar Ratio | 0.25 | 0.25 | 0.025 | — |
|  | (C) Membrane-Reinforcing Substance | Type | Cholesterol | — | Cholesterol | Cholesterol |
|  |  | Molar Ratio | 0.125 | — | 0.125 | 0.125 |
|  | Drug (Also a Fluorescent Material for Labeling) | Type | 6-Cumarin | 6-Cumarin | 6-Cumarin | 6-Cumarin |
|  |  | Molar Ratio | 0.10 mg (0.05 mg/ml) | 0.10 mg (0.05 mg/ml) | 0.10 mg (0.05 mg/ml) | 0.10 mg (0.05 mg/ml) |
| Form of Liposome After Preparation |  |  | ssLip | ssLip | ssLip | ssLip |
|  | Mean Particle Diameter |  | 108.6 (nm) | 144.8 (nm) | 144.4 (nm) | 128.0 (nm) |

Additionally, according to the same method as above, various types of liposome solutions were produced using different phospholipids as the phospholipid (A) (Example 5: DPPC ssLip, Example 6: DMPC ssLip, and Example 7: HyPC ssLip). All of these liposomes contain DCP as the charged substance (B), and contain cholesterol as the membrane-reinforcing substance (C). The proportion of the components during the preparation of these liposomes was Component A:Component B:Component C=8:2:1=1:0.25:0.125 (molar ratio). The liposome concentration (calculated as the phospholipid concentration) in the liposome solution of each of Examples 5 to 7 was 20.4 mM, which was the same as that of Examples 3 and 4.

The following tests (I) to (IV) were conducted on the liposome solutions of the Examples and Comparative Examples; the results are shown in FIGS. 2 to 6.

(I) Test for Investigating Delivery to the Posterior Segment of the Eye

Three microliters of each of the liposome solutions according to Examples 3 and 4, and Comparative Examples 1 and 2 was instilled onto the corneal surface of male 6-week-old ddY clean mice (3 mice for each group).

After predetermined periods of time (30 min, 1 hr, and 3 hr), eyeballs were enucleated, and frozen slices (thickness: 10 μm) of eyeball portions corresponding to the posterior segment of the eye shown in FIG. 1 were prepared. Fluorescence from 6-cumarin delivered to the fundus of the retina was observed under a fluorescent microscope at an excitation wavelength of 470 to 490 nm and a detection wavelength of 515 to 550 nm. The results are shown in FIG. 2.

Figure 2:
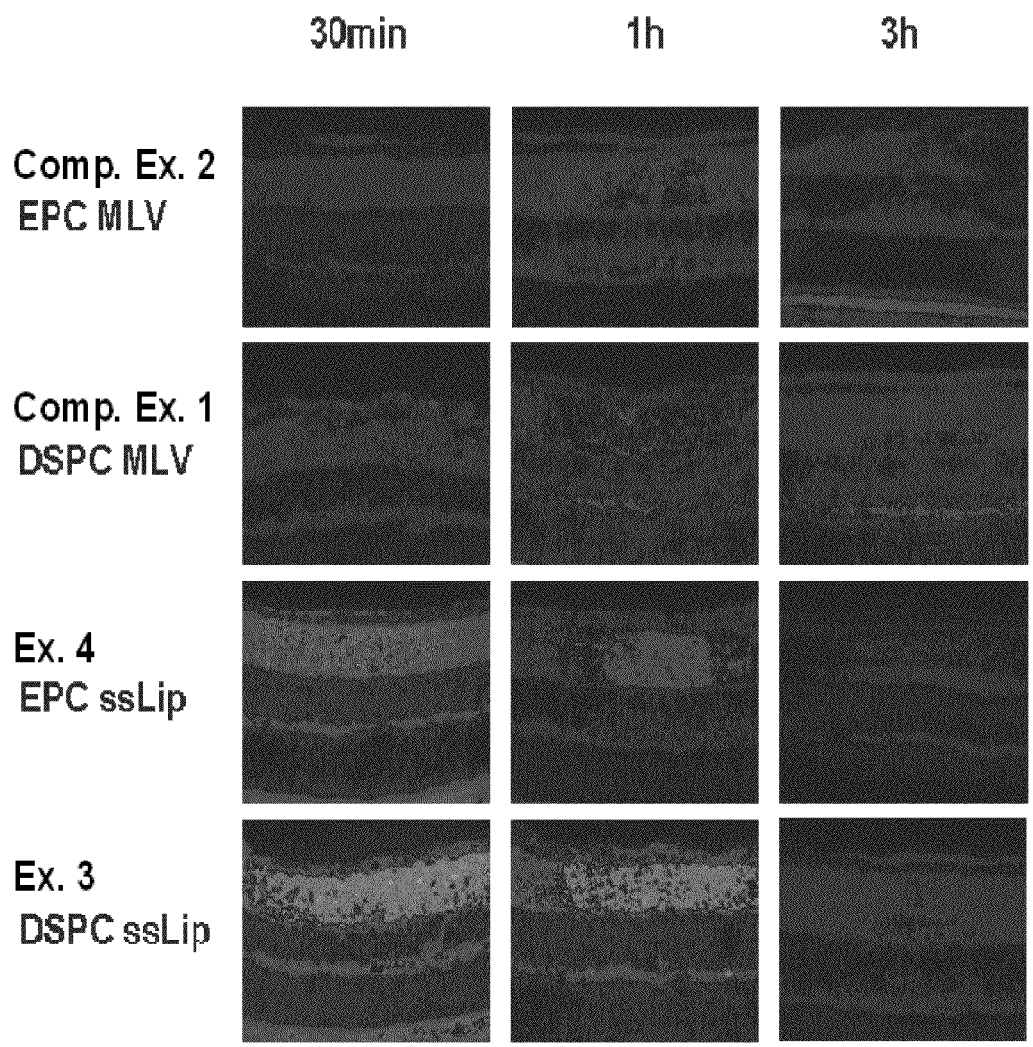
FIG. 2 shows the results of observation under a fluorescent microscope in the test for investigating delivery to the posterior segment of the eye that was conducted on the liposomes of Examples 3 and 4, and Comparative Examples 1 and 2.

FIG. 2 shows typical examples of fluorescence observed 30 minutes, 1 hour, and 3 hours after the instillation of each of the liposome solutions of Examples 3 and 4, and Comparative Examples 1 and 2.

Figure 3:
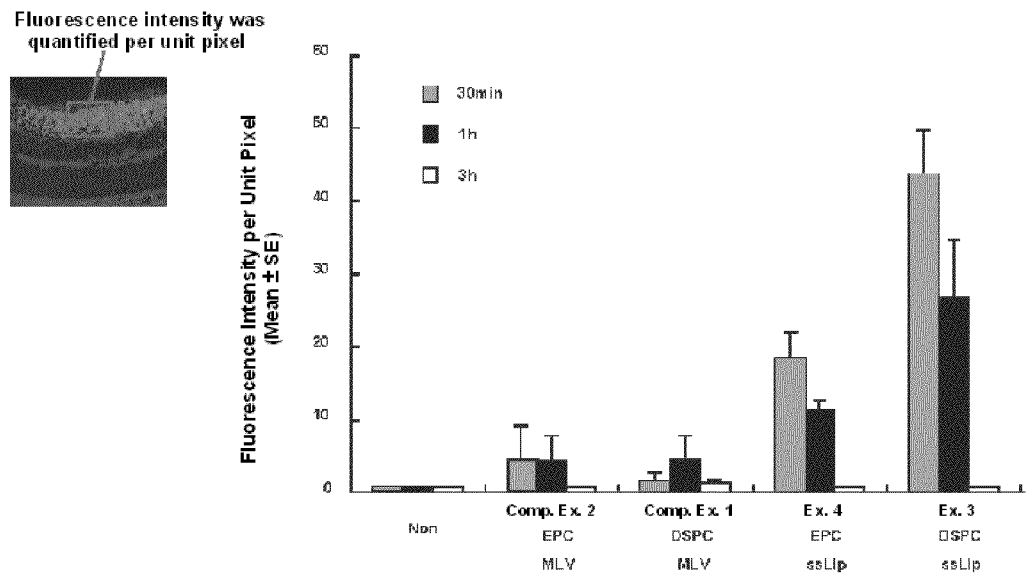
FIG. 3 is a graph showing the fluorescence intensities of FIG. 2 in numerical form.

FIG. 3 also shows fluorescence intensities quantified per unit pixel. In FIG. 3, the column "Non" denotes a control without instillation of an ophthalmic solution.

Specifically, three cases were investigated in each group (each column in the figure). The mean fluorescence intensity per unit pixel of a 50 μm square, which included the retinal ganglion cell layer and inner plexiform layer, was measured within 500 μm from the center of the optic disc (at two points on the ear-side and nose-side). The mean value at the two points was analyzed as the quantified value for each sample. The value is expressed as mean±SE, n=3.

As can be seen from FIGS. 2 and 3, delivery to the posterior segment of the eye was confirmed only for the submicron-sized liposomes with a mean particle diameter of 1 μm or less, such as DSPC ssLip of Example 3 and EPC ssLip of Example 4.

Additionally, although the data are not shown here, liposomes containing phospholipids having a high Tc, such as DSPC, even though they contained only one of the charged substance (B) and membrane-reinforcing substance (C), also showed a tendency similar to that of Example 3, although not as significantly as in Example 3.

Since the 6-cumarin used in the Examples is believed to be mixed into the liposome membranes, it is extremely likely that, in the case of the liposomes of the invention, the "liposomes themselves" were delivered to the posterior segment of the eye.

(II) Test for Investigating the Interaction Between Cells and the Liposomes (Cellular Uptake of the Liposomes)

The cellular uptake of the liposomes was assayed in vitro, using human corneal epithelial cells (HCE-T).

Each of the liposome solutions (0.5 ml) of Examples 3 to 7 having a mean particle diameter of 1 μm or less was added to a container seeded with immortalized human corneal epithelial cells (HCE-T, Cell No. RCB1384, Riken Cell Bank) at $6.3 \times 10^4$ cells/cm$^2$, and incubated for 180 minutes at 37° C.

The cultured cells were subsequently washed twice in HBSS-Hepes buffer (0.5 ml) cooled to 4° C.

The cells were then diluted with HEPES and lysed in NaOH; subsequently, by quantifying the fluorescent material (6-cumarin) incorporated into each liposome, the cellular uptake of the liposome was examined. The results are shown in FIG. 4.

The fluorescence intensity was assayed as the relative intensity, taking the fluorescence intensity of the liposome of Example 3 as 1.

Figure 4:
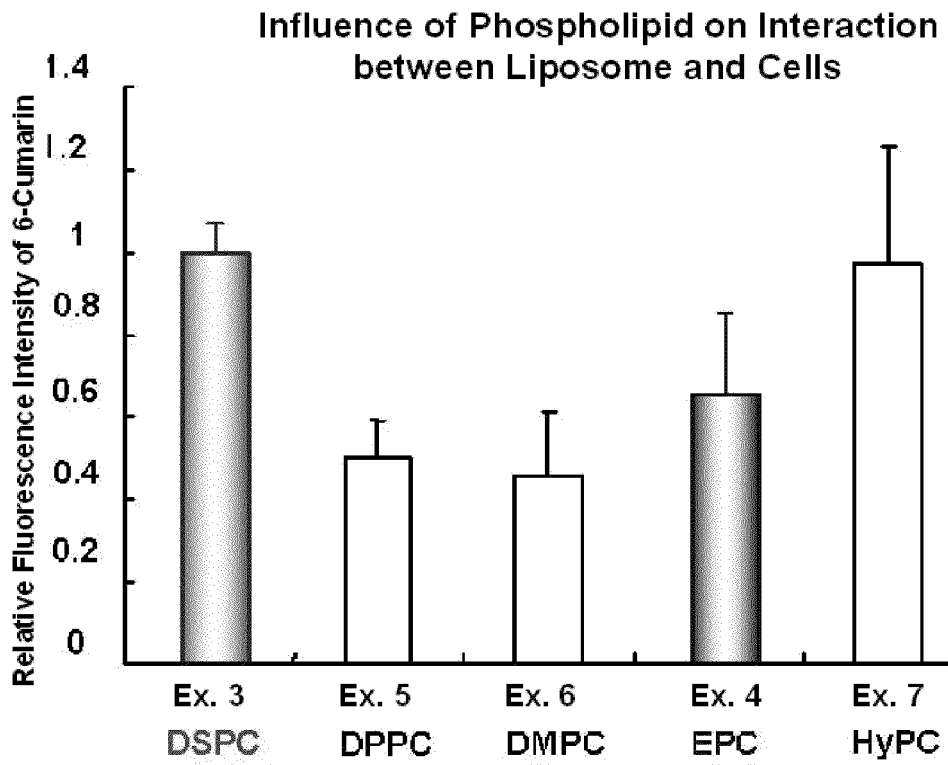
FIG. 4 is a graph showing the results of the test for investigating the interaction between cells and the liposomes (cellular uptake of the liposomes) that was conducted on the liposomes of Examples 3 to 7.

As can be seen from FIG. 4, relatively higher interactions with the cells were detected in the liposomes with a higher ability to be delivered to the posterior segment of the eye.

Further, the ability of the liposome to be delivered to the posterior segment of the eye tended to increase as the Tc of the phospholipid increased; based on the fact that, for example, DSPC of Example 3 had a Tc of about 54° C. to about 55° C., DPPC of Example 5 had a Tc of about 41° C. to about 42° C., and DMPC of Example 6 had a Tc of about 23° C. to about 24° C. In the case of EPC of Example 4, although EPC had a Tc as low as about −15° C. to about −7° C., the ability of the liposome to be delivered to the posterior segment of the eye was high. This is believed to be because the influence of the Tc is surpassed by the properties of EPC itself that easily maintain the liposome structure and easily retain the encapsulated fluorescent material (6-cumarin).

(III) Test for Investigating Toxicity (MTS Test)

Each of the liposome solutions (0.5 ml) of Examples 3 and 4 and Comparative Examples 1 and 2 was added to a container seeded with immortalized human corneal epithelial cells (HCE-T, Cell No. RCB1384, Riken Cell Bank) at $3.15 \times 10^4$ cells/cm$^2$, and incubated for 180 minutes at 37° C.

The cells were subsequently washed with HBSS, and 20 μl of the MTS reagent and 100 μl of the culture were added. The cell viability was examined by measuring the absorbance at 492 nm. The results are shown in FIG. 5.

Figure 5:
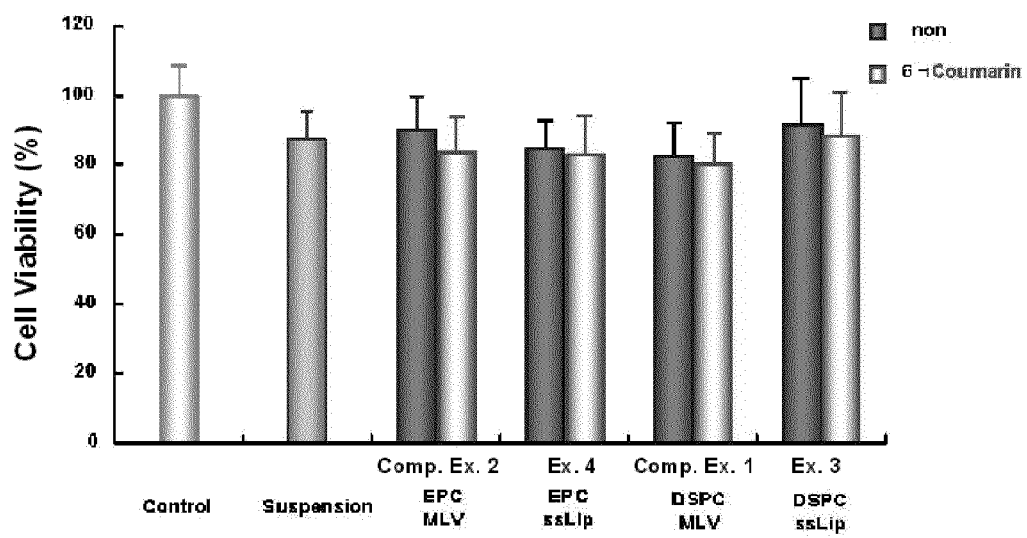
FIG. 5 is a graph showing the results of the test for investigating toxicity (MTS test) that was conducted on the liposomes of Examples 3 and 4, and Comparative Examples 1 and 2.

In FIG. 5, "Control" denotes HBSS-Hepes buffer, and "Suspension" denotes a suspension of 6-cumarin only.

The MTS reagent means 3-(4,5-dimethylthiazol-2-yl)-5-(3-carboxymethoxyphenyl)-2-(4-sulfophenyl)-2H-tetorazolium inner salt.

The MTS test utilizes the fact that the amount of a formazan product produced by mitochondria is proportional to the number of viable cells in the culture. In the MTS test, assuming that "[A] control" is the amount of the formazan product for a control obtained by adding only a cell-maintenance solution (HEPES-HBSS) to cultured cells, and that "[A]test" is the amount of the formazan product for cells to which each of the test materials (i.e., the liposomes of the Examples and Comparative Examples) was added, the ratio of "[A]test" to the "[A]control" was determined as the cell viability (%) according to the equation shown below.

The amount of the formazan product was measured by reading the absorbance at 490 nm.

$$[A]test/[A]control \times 100$$

As can be seen from FIG. 5, all of the liposomes showed little cytotoxicity, indicating that cytotoxicity is not the cause of delivery to the posterior segment of the eye. At the same time, these results also indicate the safety of the liposomes of the invention when they are used as drug carriers.

(IV) Test for Investigating Delivery to the Posterior Segment of the Eye Using Rabbits Fifty microliters of the liposome solution of Example 3 (DSPC ssLip) was instilled into the eyes of rabbits (18 male Japanese white rabbits, 2.5 kg). Before instillation (i.e., untreated), and 10 minutes, 30 minutes, 1 hour, 2 hours, and 6 hours after the instillation, eyeballs were enucleated, slices were prepared therefrom, and the fluorescence intensities of 6-cumarin were observed.

Figure 6:
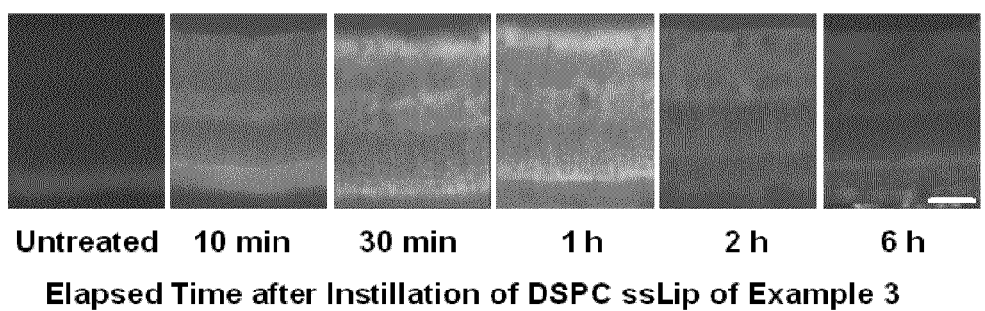
FIG. 6 shows the results of observation under a fluorescent microscope in the test for investigating delivery to the posterior segment of the eye using rabbits that was conducted on the liposome of Example 3.

The results are shown in FIG. 6.

Figure 7:
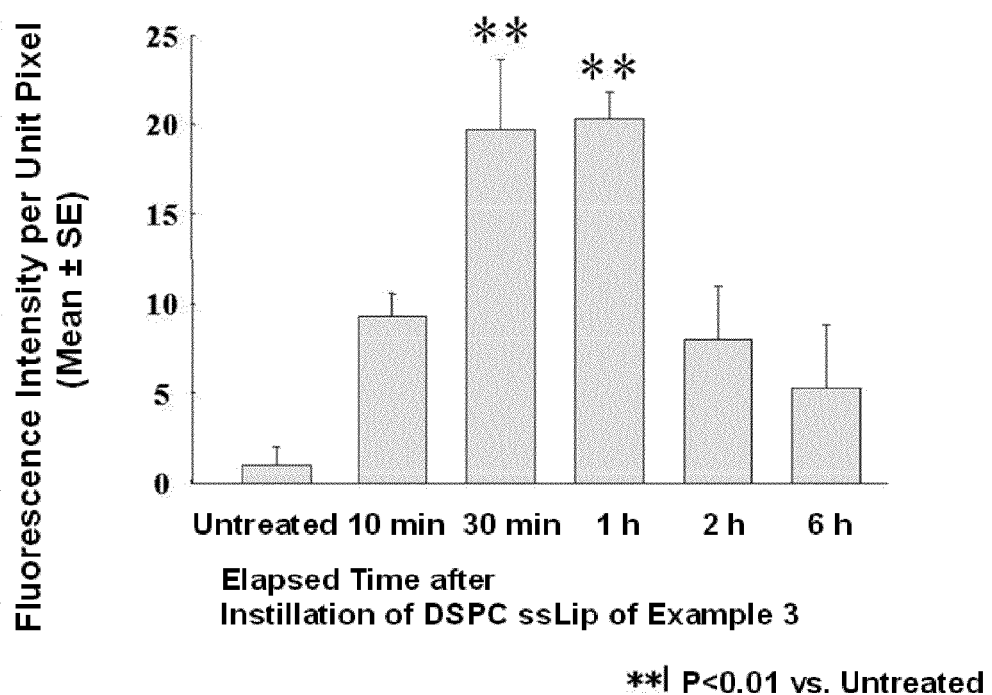
FIG. 7 is a graph showing the fluorescence intensities of FIG. 6 in numerical form.
Figure 8:
FIG. 8 shows the result of observation under a fluorescent microscope in the test for investigating delivery to the posterior segment of the eye that was conducted on the liposome of Example 8.
Figure 9:
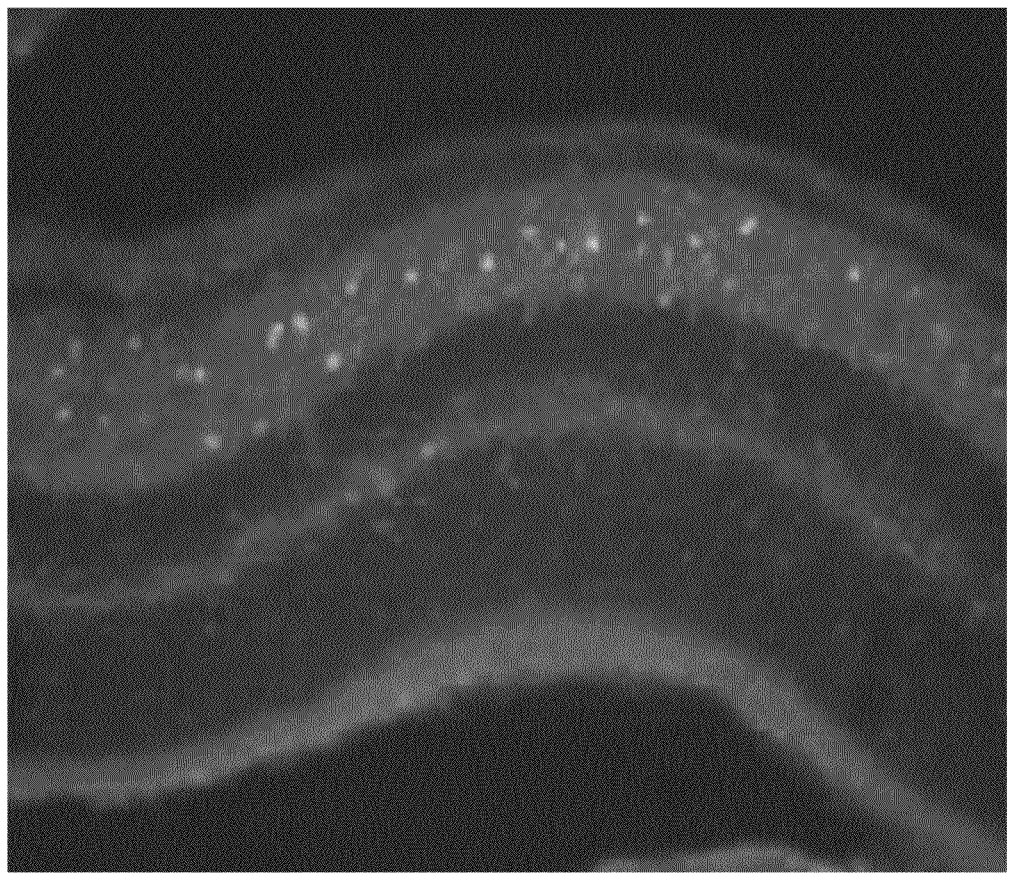
FIG. 9 shows the result of observation under a fluorescent microscope in the test for investigating delivery to the posterior segment of the eye that was conducted on the liposome of Example 9.
Figure 10:
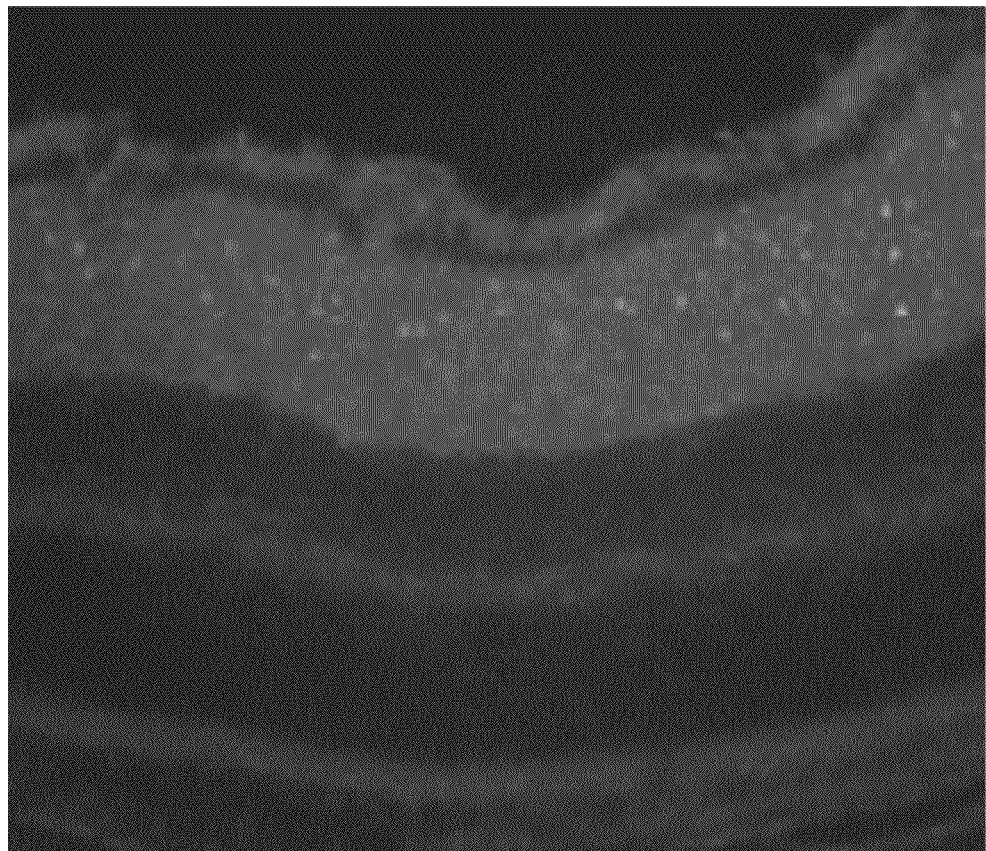
FIG. 10 shows the result of observation under a fluorescent microscope in the test for investigating delivery to the posterior segment of the eye that was conducted on the liposome of Example 10.
Figure 11:
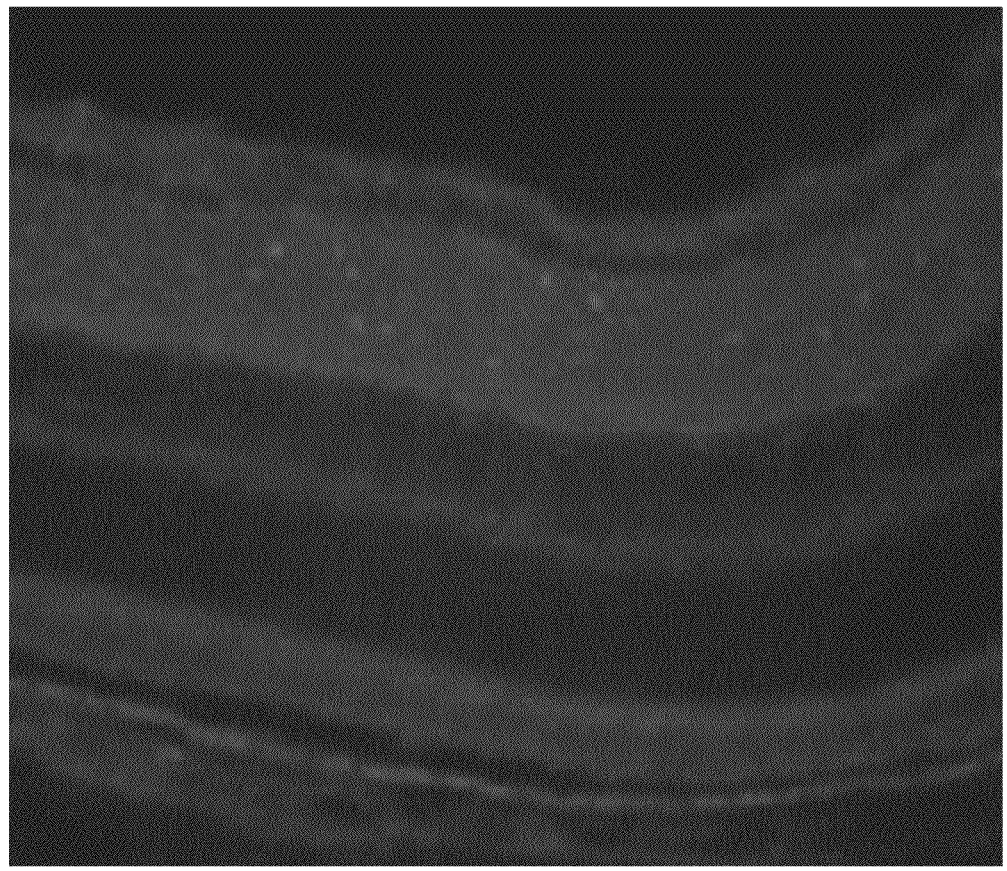
FIG. 11 shows the result of observation under a fluorescent microscope in the test for investigating delivery to the posterior segment of the eye that was conducted on the liposome of Example 11.

FIG. 7 also shows fluorescence intensities quantified per unit pixel.

Specifically, three cases were investigated in each group (each column in the figure). The mean fluorescence intensity per unit pixel of a 50 μm square, which included the retinal ganglion cell layer and inner plexiform layer, was measured within 500 μm from the center of the optic disc (at two points on the ear-side and nose-side). The mean value at the two points was analyzed as the quantified value for each sample. The value is expressed as mean±SE, n=3.

As can be seen from FIGS. 6 and 7, the delivery of the DSPC liposome having a mean particle diameter of 1 μm or less to the posterior segment of the eye was also confirmed in rabbits.

Examples 8 to 11

Following the method described in the Examples above and the like, liposomes having a molar ratio of DSPC/DCP/Chol.=8/2/1=1/0.25/0.125 were prepared. In the purification process of these liposomes, the pore size of the membrane filter used for extrusion was varied, thereby producing solutions containing liposomes having mean particle diameters of 116.8 nm (Example 8), 174.8 nm (Example 9), 300.6 nm (Example 10), and 561.0 nm (Example 11). The solutions containing these liposomes all had a liposome concentration (a phospholipid concentration) of 20.4 mM.

The test (I) for investigating delivery to the posterior segment of the eye was conducted on these liposome solutions. According to the results, all of the liposome solutions migrated to the posterior segment of the eye. However, the amount of each liposome solution delivered tended to depend on the mean particle diameter of the liposome (FIGS. 8 to 11).

That is to say, these results indicate that the ability of the liposome to be delivered to the posterior segment of the eye tends to increase as the mean particle diameter of the liposome becomes smaller.

Example 12

Following the methods described in the above examples and the like, a solution containing a liposome having a compositional ratio (a molar ratio) of EPC/SA/Chol.=7/1/3≈1/0.14/0.43, and having an H/P=0.15 (H=15.3±1.17, P=103.635±0.85), was prepared.

Figure 12:
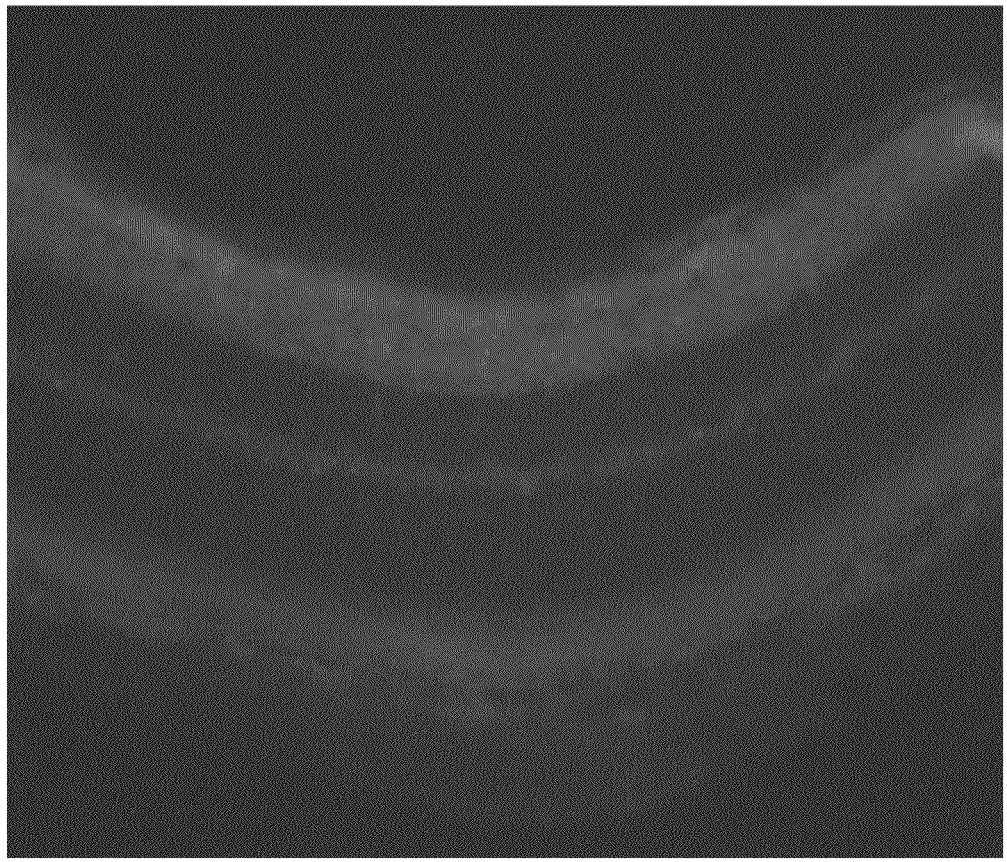
FIG. 12 shows the result of observation under a fluorescent microscope in the test for investigating delivery to the posterior segment of the eye that was conducted on the liposome of Example 12.
Figure 13:
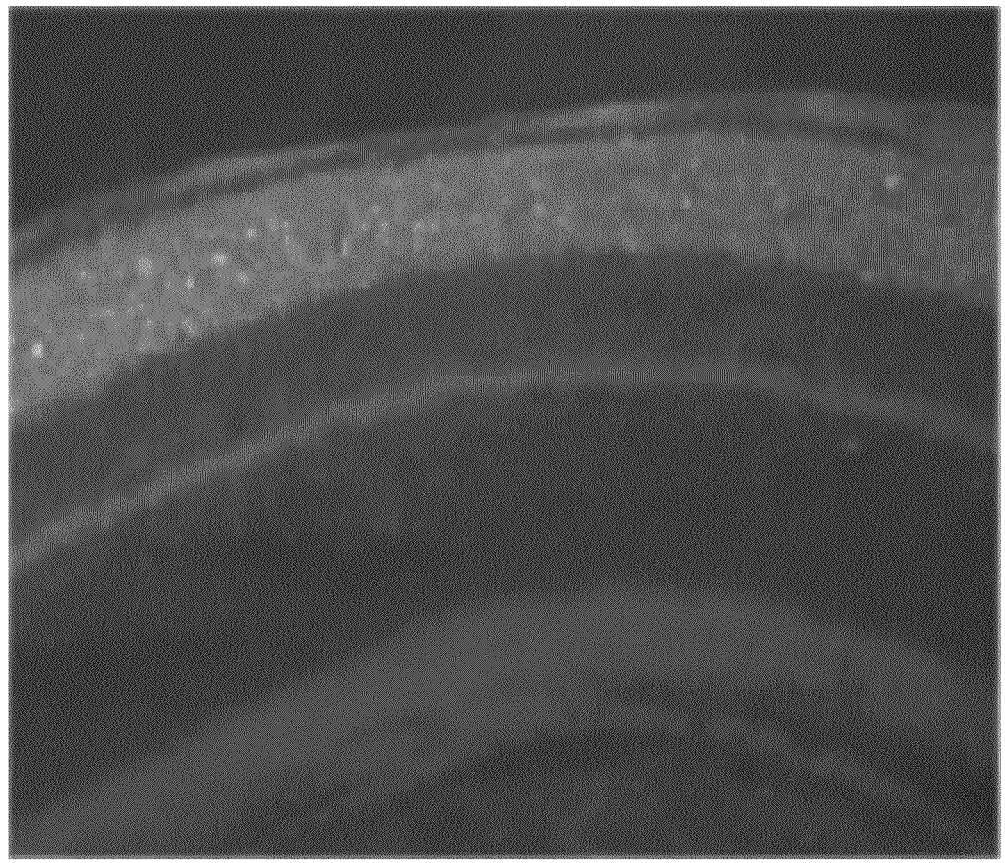
FIG. 13 shows the result of observation under a fluorescent microscope in the test for investigating delivery to the posterior segment of the eye that was conducted on the liposome of Example 13.
Figure 14:
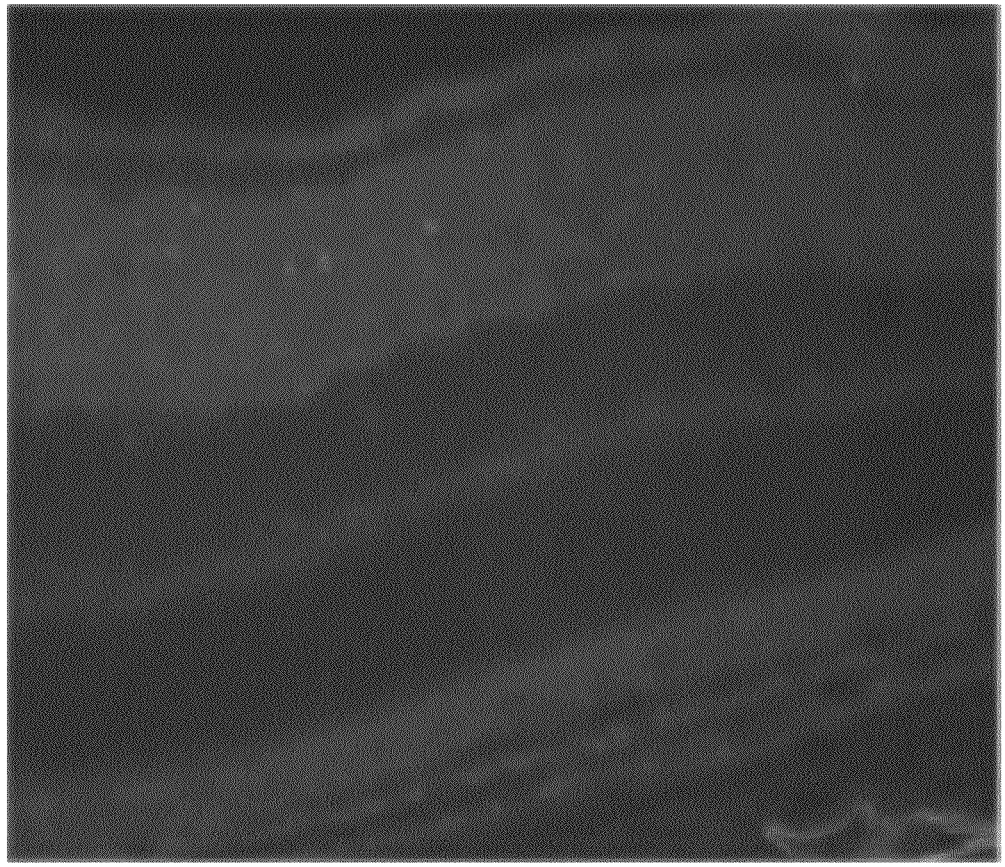
FIG. 14 shows the result of observation under a fluorescent microscope in the test for investigating delivery to the posterior segment of the eye that was conducted on the liposome of Example 14.
Figure 15:
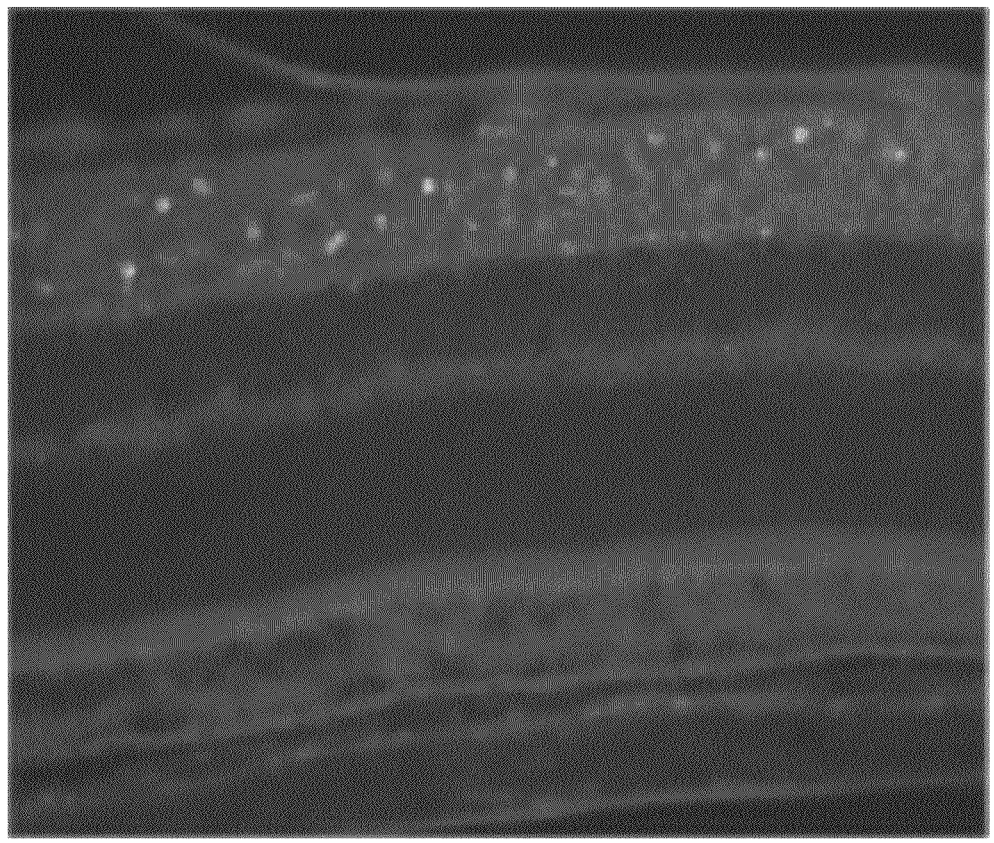
FIG. 15 shows the result of observation under a fluorescent microscope in the test for investigating delivery to the posterior segment of the eye that was conducted on the liposome of Example 15.
Figure 16:
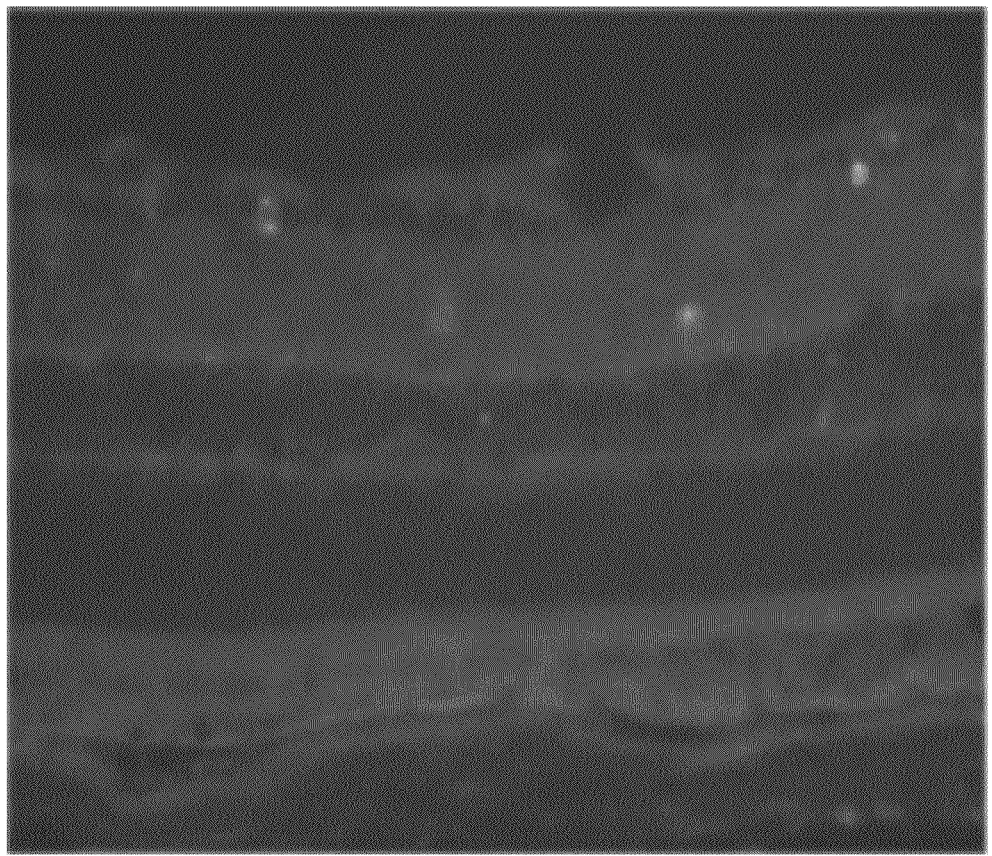
FIG. 16 shows the result of observation under a fluorescent microscope in the test for investigating delivery to the posterior segment of the eye that was conducted on the liposome of Example 16.

The test (I) for investigating delivery to the posterior segment of the eye was conducted on this liposome. As a result, the delivery of the liposome to the posterior segment of the eye was confirmed (FIG. 12).

Examples 13 to 16

Following the method described in the Examples above and the like, solutions containing various liposomes were prepared using the compositional ratios shown in Table 3.

TABLE 3

| | | | Ex. 13 | Ex. 14 | Ex. 15 | Ex. 16 |
|---|---|---|---|---|---|---|
| Preparation Composition | (A) Phospholipid | Type | DSPC | DSPC | DSPC | DSPC |
| | | Molar Ratio | 1 | 1 | 1 | 1 |
| | (B) Charged Substance | Type | DCP | DCP | SA | — |
| | | Molar Ratio | 0.25 | 0.25 | 0.025 | — |
| | (C) Membrane-Reinforcing Substance | Type | Cholesterol | — | Cholesterol | Cholesterol |
| | | Molar Ratio | 0.125 | — | 0.125 | 0.125 |
| | Drug (Also a Fluorescent Material for Labeling) | Type | 6-Cumarin | 6-Cumarin | 6-Cumarin | 6-Cumarin |
| | | Molar Ratio | 0.10 mg (0.05 mg/ml) | 0.10 mg (0.05 mg/ml) | 0.10 mg (0.05 mg/ml) | 0.10 mg (0.05 mg/ml) |
| Form of Liposome After Preparation | | | ssLip | ssLip | ssLip | ssLip |
| | Mean Particle Diameter | | 108.6 (nm) | 144.8 (nm) | 144.4 (nm) | 128.0 (nm) |

The test (I) for investigating delivery to the posterior segment of the eye was conducted on these liposomes. As a result, the delivery of the liposomes to the posterior segment of the eye was confirmed. However, the liposomes of Examples 13 and 15, each containing both Components (B) and (C), were delivered in high proportions, compared to the liposome of Example 14, which did not contain the membrane-reinforcing substance (C), and the liposome of Example 16, which did not contain the charged substance (B).

Comparative Example 3

The liposomes were replaced with a suspension obtained by adding 10% (v/v) of a 50% (w/v) glucose solution to polystyrene particles fluorescently labeled with FITC (Micromer-greenF (registered trademark), manufactured by Corefront Corporation, mean particle diameter: 110.7 nm), and by making the resulting suspension isotonic by adjusting the final concentration of glucose in the suspension to 5% (w/v).

The polystyrene particles had a rigidity (H/P) of about 1.0.

Figure 17:
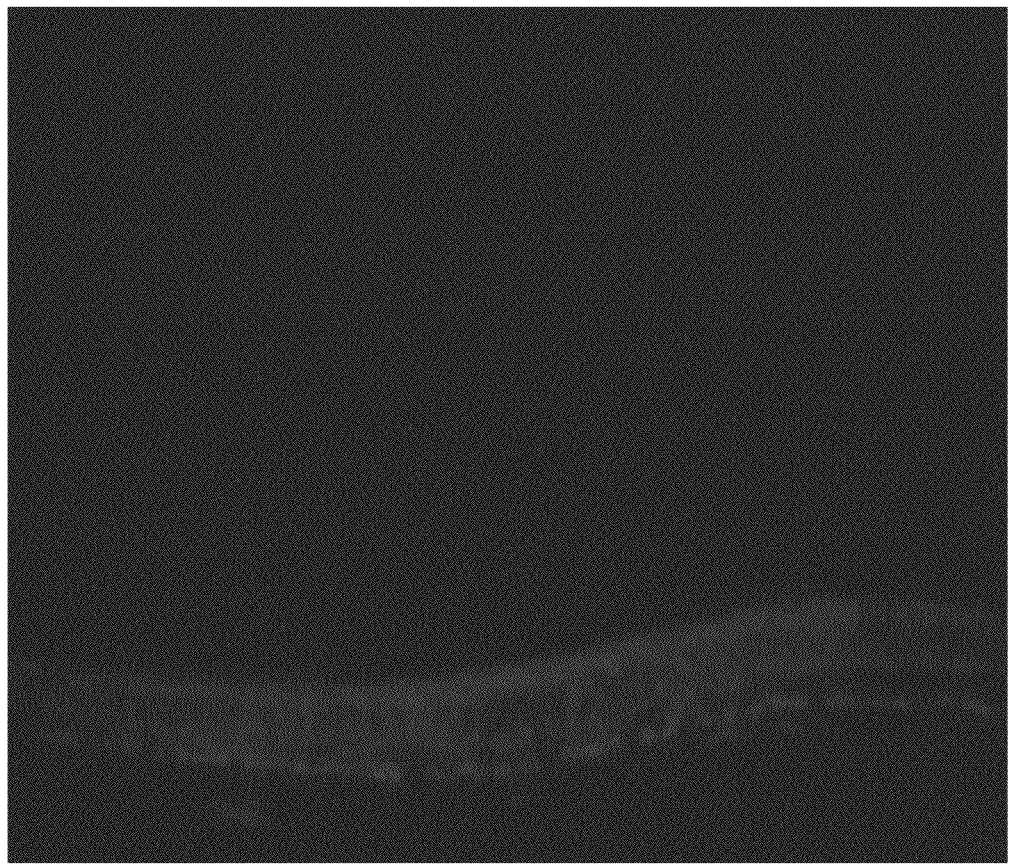
FIG. 17 shows the result of observation under a fluorescent microscope in the test for investigating delivery to the posterior segment of the eye that was conducted on the FITC-labeled polystyrene particles of Comparative Example 3.

However, according to the results of the test (I) for investigating delivery to the posterior segment of the eye that was conducted on these polystyrene particles, the particles did not migrate to the posterior segment of the eye at all (FIG. 17).

This result indicates that not only the rigidity and size of the particles, but also the components forming the particles are important, in order to enable the delivery to the posterior segment of the eye.

(V) Second Test for Investigating Delivery to the Posterior Segment of the Eye

Figure 18:
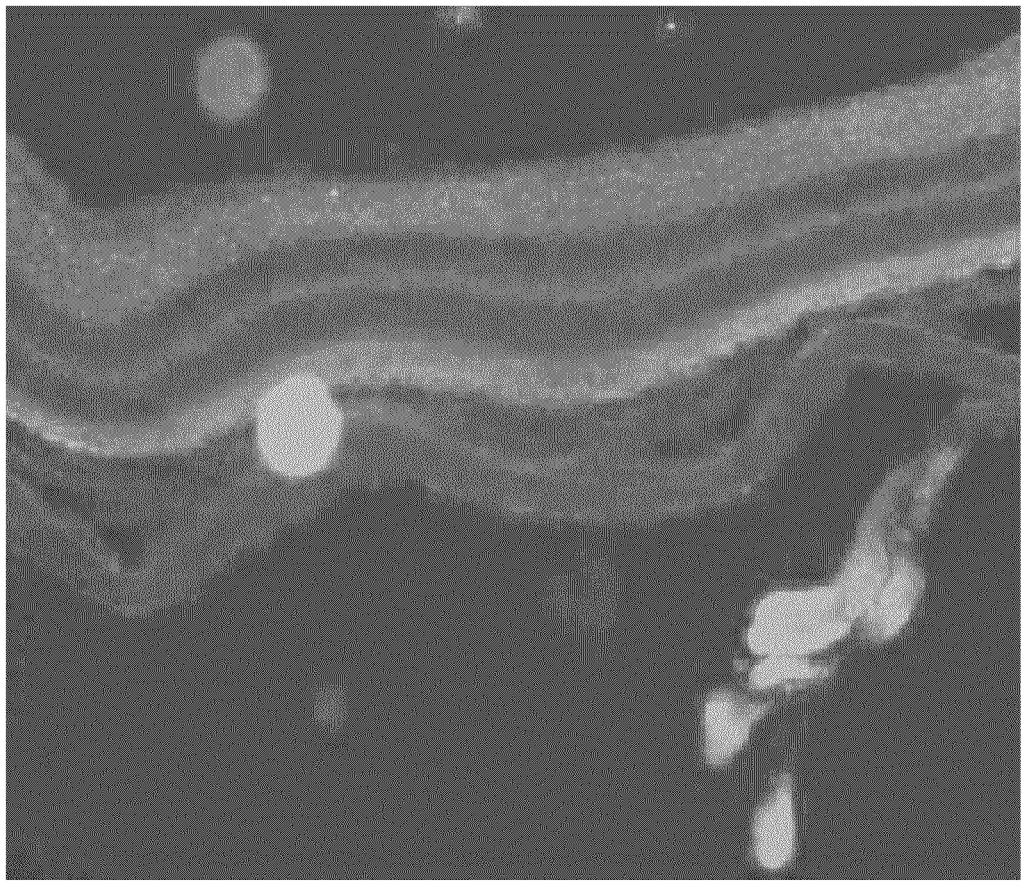
FIG. 18 shows the result of observation under a fluorescent microscope in the test for investigating delivery to the posterior segment of the eye that was conducted on the liposome of Example 5.
Figure 19:
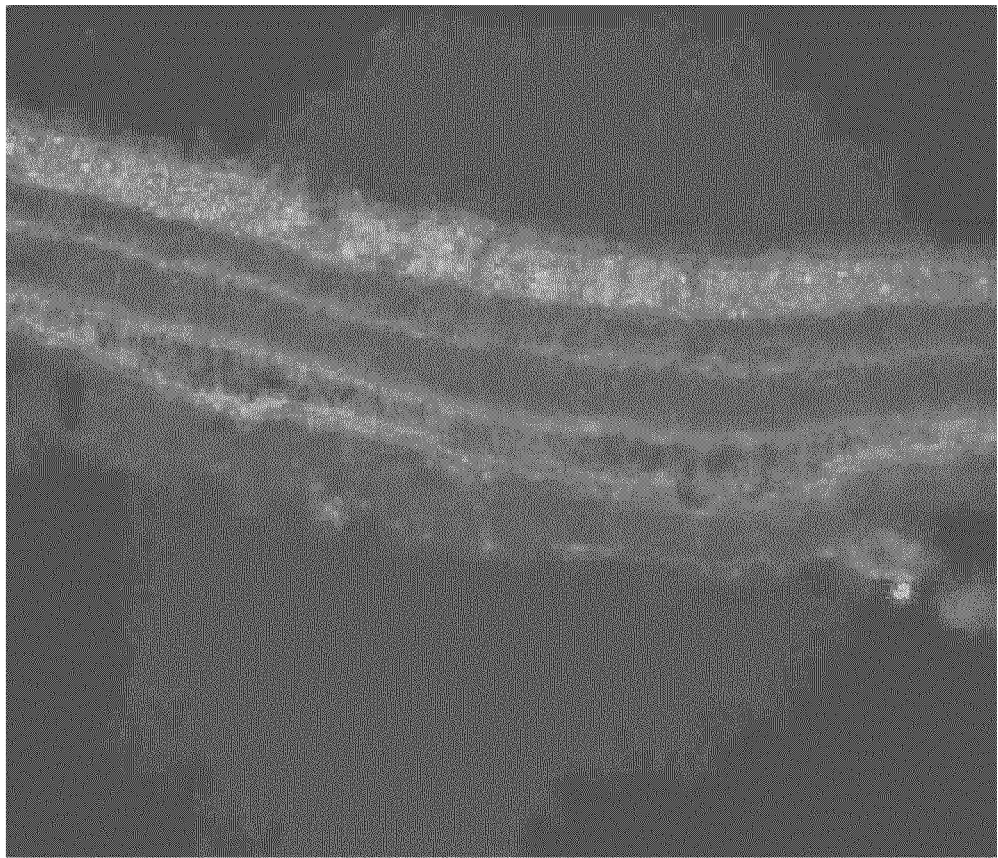
FIG. 19 shows the result of observation under a fluorescent microscope in the test for investigating delivery to the posterior segment of the eye that was conducted on the liposome of Example 6.

Three microliters of each of the liposome solutions of Example 5 (DPPC ssLip, 114.1 nm) and Example 6 (DMPC ssLip, 124.7 nm) was instilled into the eyes of mice in the same method as the test (I) for investigating delivery to the posterior segment of the eye. The results of observation under a fluorescent microscope 30 minutes after the instillation are shown in FIGS. 18 and 19.

As can be seen from these figures, among the liposomes of Examples 3 to 7, delivery to the posterior segment of the eye in living mice was also confirmed for the liposome of Example 5 (DPPC ssLip) and the liposome of Example 6 (DMPC ssLip), both of which had lower interaction with the cells (see FIG. 4).

INDUSTRIAL APPLICABILITY

The liposome of the invention is capable of delivery to the posterior segment of the eye, and hence, is suitably used for non-invasive prevention or treatments, such as topical applications including instillation, as a pharmaceutical composition for a disease in the posterior segment of the eye.

The invention claimed is:

1. A method for treating a disease in the posterior segment of the eye, comprising administering locally to the eye of a subject having a disease in the posterior segment a pharmaceutical composition which is in a form of an ophthalmic solution or an ophthalmic ointment and comprises a liposome encapsulating a drug, wherein the liposome comprises
    (A) at least one phospholipid selected from the group consisting of distearoylphosphatidylcholine, dipalmitoylphosphatidylcholine, dimyristoylphosphatidylcholine, dilauroylphosphatidylcholine, egg phosphatidylcholine, and hydrogenated phosphatidylcholine,
    (B) at least one negatively charged substance selected from the group consisting of dicetyl phosphate, and dipalmitoylphosphatidylglycerol, and
    (C) a membrane-reinforcing substance; and wherein the liposome has a rigidity that provides the liposome with cell membrane permeability and a mean particle diameter of 1 μm or less, and wherein the disease in the posterior segment of the eye is at least one disease selected from the group consisting of age-related macular degeneration, diabetic retinopathy, and uveitis, thereby treating a disease in the posterior segment of the eye, and
    wherein the drug is at least one drug selected from the group consisting of carteolol hydrochloride, nipradilol, dorzolamide hydrochloride, acetazolamide, glutathione, memantine, fluorometholone, prednisolone, betamethasone, dexamethasone, indomethacin, dichlofenac sodium, and bromfenac sodium.

2. The method for treating a disease in the posterior segment of the eye according to claim 1, wherein the rigidity that provides the liposome with cell membrane permeability is an H/P value of 0.15 to 1.0 according to Expression (I):

$$H/P \tag{I}$$

wherein H represents a height of the liposome adsorbed on a substrate, as measured by atomic force microscopy; and
P represents a mean particle diameter of the liposome, as measured by dynamic light scattering.

3. The method for treating a disease in the posterior segment of the eye according to claim 1, wherein the mean particle diameter is 600 nm or less.

4. The method for treating a disease in the posterior segment of the eye according to claim 1, wherein liposome particles have a gel to liquid-crystalline phase transition temperature of 20° C. or more.

5. The method for treating a disease in the posterior segment of the eye according to claim 1, wherein Component (C) is at least one compound having a steroid skeleton, wherein the compound is selected from the group consisting of cholesterol, dihydrocholesterol, cholesteryl esters, cholestanol, dehydrocholesterol, cholesteryl lanolates, cholesteryl isostearate, cholesteryl 12-hydroxystearate, cholesteryl ricinoleate, cholesteryl macadamiates, phytosterol, sitosterol, stigmasterol, campesterol, lanosterol, 2,4-dihydrolanosterol, 1-O-sterol glucosides, 1-O-sterol maltosides, and 1-O-sterol galactosides.

6. The method for treating a disease in the posterior segment of the eye according to claim 1, wherein the liposome is a submicron sized small uni-lamellar vesicle.

* * * * *